United States Patent
Akbarian et al.

(10) Patent No.: US 12,213,737 B2
(45) Date of Patent: Feb. 4, 2025

(54) USER INTERFACE FOR IMAGE GUIDED SURGERY SYSTEM

(71) Applicants: Acclarent, Inc., Irvine, CA (US); Biosense Webster (Israel) Ltd., Yokneam (IL)

(72) Inventors: Fatemeh Akbarian, Rancho Palos Verdes, CA (US); Athanasios Papadakis, Newport Beach, CA (US); Jordan R. Trott, Redondo Beach, CA (US); Noam Racheli, Hadera (IL); Itamar Bustan, Zichron Ya'acov (IL); Jetmir Palushi, Irvine, CA (US)

(73) Assignees: Acclarent, Inc., Irvine, CA (US); Biosense Webster (Israel) Ltd., Yokneam (IL)

( * ) Notice: Subject to any disclaimer, the term of this patent is extended or adjusted under 35 U.S.C. 154(b) by 930 days.

(21) Appl. No.: 17/194,466

(22) Filed: Mar. 8, 2021

(65) Prior Publication Data
US 2021/0315636 A1     Oct. 14, 2021

Related U.S. Application Data

(60) Provisional application No. 63/007,713, filed on Apr. 9, 2020.

(51) Int. Cl.
*A61B 34/10*   (2016.01)
*A61B 34/00*   (2016.01)
*A61B 34/20*   (2016.01)

(52) U.S. Cl.
CPC ............. *A61B 34/10* (2016.02); *A61B 34/20* (2016.02); *A61B 34/25* (2016.02);
(Continued)

(58) Field of Classification Search
CPC ......... A61B 34/10; A61B 34/20; A61B 34/25; A61B 2034/105; A61B 2034/107; A61B 2034/2057; A61B 2034/2068
See application file for complete search history.

(56) References Cited

U.S. PATENT DOCUMENTS

| | | | |
|---|---|---|---|
| 7,720,521 B2 | 5/2010 | Chang et al. | |
| 10,463,242 B2 | 11/2019 | Kesten et al. | |

(Continued)

FOREIGN PATENT DOCUMENTS

EP     2973424 B1     2/2018

OTHER PUBLICATIONS

Extended European Search Report dated Sep. 3, 2021, for Application No. 21167302.5, 9 pages.

*Primary Examiner* — Kibrom K Gebresilassie
(74) *Attorney, Agent, or Firm* — Barnes & Thornburg LLP

(57) ABSTRACT

A virtual camera may be positioned relative to a 3-D model of a patient anatomy in order to provide a virtual camera view of the surrounding anatomy and tracked surgical instruments being deployed to the anatomy. Visual context provided by the virtual camera may be limited in some cases, such as where a surgical instrument is being used within a very narrow anatomical passageway or cavity. To provide more placement flexibility, an IGS system providing a virtual camera receives inputs defining variable visual characteristics for different segments or regions of the 3-D model, which may include hiding certain segments or making certain segments semi-transparent. With such a system, the view of the 3-D model provided by the virtual camera view may be modified to remove or deemphasize less relevant segments, to display or emphasize more relevant segments (e.g., critical patient anatomy), or both.

20 Claims, 5 Drawing Sheets

(52) U.S. Cl.
CPC ... *A61B 2034/105* (2016.02); *A61B 2034/107* (2016.02); *A61B 2034/2057* (2016.02); *A61B 2034/2068* (2016.02)

(56) References Cited

U.S. PATENT DOCUMENTS

| | | |
|---|---|---|
| 10,561,370 B2 | 2/2020 | Salazar et al. |
| 2014/0364725 A1 | 12/2014 | Makower |
| 2018/0161102 A1* | 6/2018 | Wei .................. A61B 34/10 |
| 2019/0133694 A1* | 5/2019 | Barrera ............. A61B 34/10 |
| 2019/0159842 A1* | 5/2019 | Razeto .............. G06T 7/33 |
| 2019/0272634 A1* | 9/2019 | Li ..................... G06T 7/0012 |
| 2019/0320878 A1* | 10/2019 | Duindam ........... G06T 7/30 |

\* cited by examiner

USER INTERFACE FOR IMAGE GUIDED SURGERY SYSTEM

PRIORITY

This application claims priority to U.S. Provisional Pat. App. No. 63/007,713, entitled "User Interface for Image Guided Surgery System," filed Apr. 9, 2020, the disclosure of which is incorporated by reference herein.

BACKGROUND

Image-guided surgery (IGS) is a technique where a computer is used to obtain a real-time correlation of the location of an instrument that has been inserted into a patient's body to a set of preoperatively obtained images (e.g., a CT or MRI scan, 3-D map, etc.), such that the computer system may superimpose the current location of the instrument on the preoperatively obtained images. An example of an electromagnetic IGS navigation systems that may be used in IGS procedures is the CARTO® 3 System by Biosense-Webster, Inc., of Irvine, California. In some IGS procedures, a digital tomographic scan (e.g., CT or MM, 3-D map, etc.) of the operative field is obtained prior to surgery. A specially programmed computer is then used to convert the digital tomographic scan data into a digital map. During surgery, special instruments having sensors (e.g., electromagnetic coils that emit electromagnetic fields and/or are responsive to externally generated electromagnetic fields) are used to perform the procedure while the sensors send data to the computer indicating the current position of each surgical instrument. The computer correlates the data it receives from the sensors with the digital map that was created from the preoperative tomographic scan. The tomographic scan images are displayed on a video monitor along with an indicator (e.g., crosshairs or an illuminated dot, etc.) showing the real-time position of each surgical instrument relative to the anatomical structures shown in the scan images. The surgeon is thus able to know the precise position of each sensor-equipped instrument by viewing the video monitor even if the surgeon is unable to directly visualize the instrument itself at its current location within the body.

Some IGS systems may additionally display three-dimensional renderings or 3-D models of patient anatomy that are based on preoperatively obtained images or other data sources. Such a 3-D model may be displayed in addition to one or more two-dimensional image slices in order to provide a surgeon additional tools to in visualizing and navigating the patient anatomy. One way in which a 3-D model may be navigated is by the use of a virtual camera feature that provides a corresponding virtual endoscopic view. A virtual camera may be positioned and oriented relative to the 3-D model in order to provide a virtual endoscopic view of the 3-D model that simulates the field of view that would be provided by a real endoscope placed at the same position and orientation. This virtual endoscopic view may be combined with representations of real-time positions of sensor-equipped instruments in order to provide the surgeon with additional visual details during a procedure.

While several systems and methods have been made and used in surgical procedures, it is believed that no one prior to the inventors has made or used the invention described in the appended claims.

BRIEF DESCRIPTION OF THE DRAWINGS

While the specification concludes with claims which particularly point out and distinctly claim the invention, it is believed the present invention will be better understood from the following description of certain examples taken in conjunction with the accompanying drawings, in which like reference numerals identify the same elements and in which:

Figure 1:
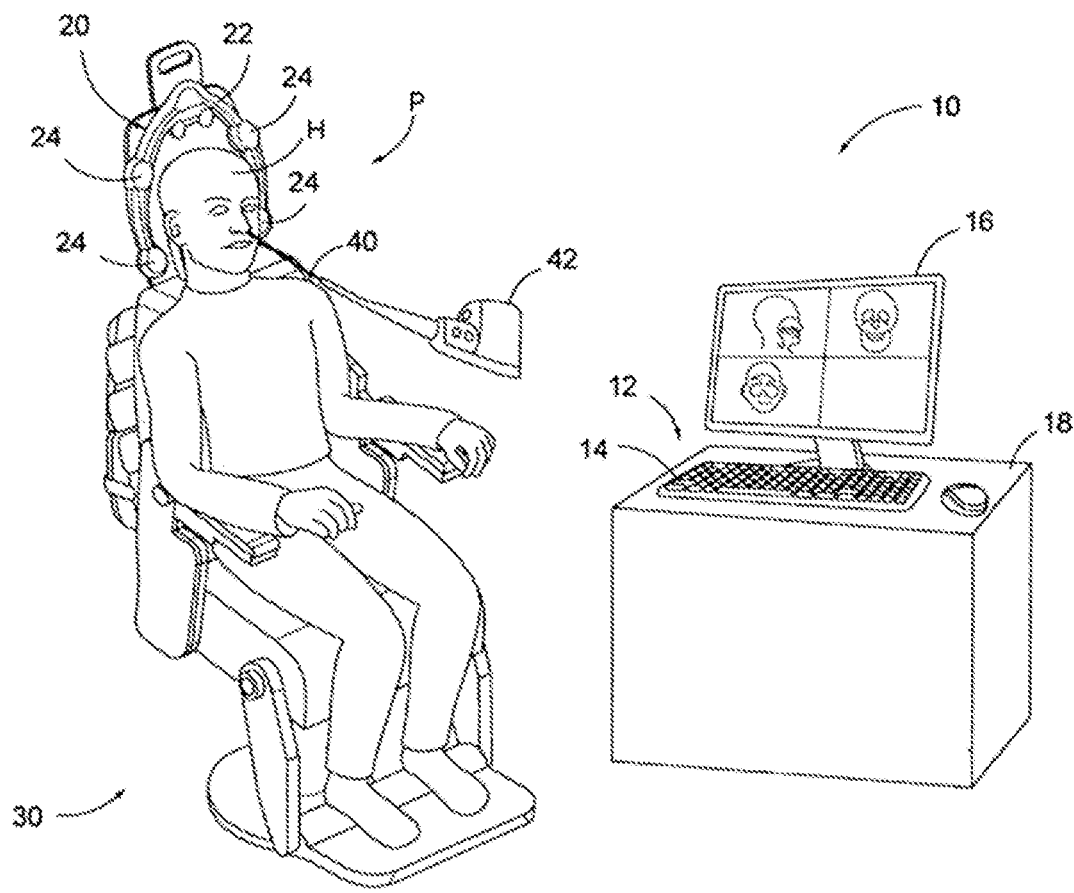
FIG. 1 depicts a schematic view of an exemplary surgery navigation system being used on a patient.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

It will be appreciated that the terms "proximal" and "distal" are used herein with reference to a clinician gripping a handpiece assembly. Thus, an end effector is distal with respect to the more proximal handpiece assembly. It will be further appreciated that, for convenience and clarity, spatial terms such as "top" and "bottom" also are used herein with respect to the clinician gripping the handpiece assembly. However, surgical instruments are used in many orientations and positions, and these terms are not intended to be limiting and absolute.

It is further understood that any one or more of the teachings, expressions, versions, examples, etc. described herein may be combined with any one or more of the other teachings, expressions, versions, examples, etc. that are described herein. The following-described teachings, expressions, versions, examples, etc. should therefore not be viewed in isolation relative to each other. Various suitable ways in which the teachings herein may be combined will be readily apparent to those skilled in the art in view of the teachings herein. Such modifications and variations are intended to be included within the scope of the claims.

I. EXEMPLARY IMAGE GUIDED SURGERY NAVIGATION SYSTEM

When performing a medical procedure within a head (H) of a patient (P), it may be desirable to have information regarding the position of an instrument within the head (H) of the patient (P), particularly when the instrument is in a location where it is difficult or impossible to obtain an endoscopic view of a working element of the instrument within the head (H) of the patient (P). FIG. 1 shows an exemplary IGS navigation system (10) enabling an ENT procedure to be performed using image guidance. In addition to or in lieu of having the components and operability described herein IGS navigation system (10) may be constructed and operable in accordance with at least some of the teachings of U.S. Pat. No. 7,720,521, entitled "Methods and Devices for Performing Procedures within the Ear, Nose, Throat and Paranasal Sinuses," issued May 18, 2010, the disclosure of which is incorporated by reference herein; and U.S. Pat. Pub. No. 2014/0364725, entitled "Systems and Methods for Performing Image Guided Procedures within the Ear, Nose, Throat and Paranasal Sinuses," published Dec. 11, 2014, now abandoned, the disclosure of which is incorporated by reference herein.

IGS navigation system (10) of the present example comprises a field generator assembly (20), which comprises set of magnetic field generators (24) that are integrated into a horseshoe-shaped frame (22). Field generators (24) are operable to generate alternating magnetic fields of different frequencies around the head (H) of the patient (P) to produce a tracked area that the IGS navigation system (10) associates a coordinate system with. A navigation guidewire (40) is inserted into the head (H) of the patient (P) in this example. Navigation guidewire (40) may be a standalone device or may be positioned on an end effector or other location of a medical instrument such as a surgical cutting instrument or dilation instrument. In the present example, frame (22) is mounted to a chair (30), with the patient (P) being seated in the chair (30) such that frame (22) is located adjacent to the head (H) of the patient (P). By way of example only, chair (30) and/or field generator assembly (20) may be configured and operable in accordance with at least some of the teachings of U.S. Pat. No. 10,561,370, entitled "Apparatus to Secure Field Generating Device to Chair," issued Feb. 18, 2020, the disclosure of which is incorporated by reference herein.

IGS navigation system (10) of the present example further comprises a processor (12), which controls field generators (24) and other elements of IGS navigation system (10). For instance, processor (12) is operable to drive field generators (24) to generate alternating electromagnetic fields; and process signals from navigation guidewire (40) to determine the location of a sensor in navigation guidewire (40) within the head (H) of the patient (P). Processor (12) comprises a processing unit (e.g., a set of electronic circuits arranged to evaluate and execute software instructions using combinational logic circuitry or other similar circuitry) communicating with one or more memories. Processor (12) of the present example is mounted in a console (18), which comprises operating controls (14) that include a keypad and/or a pointing device such as a mouse or trackball. A physician uses operating controls (14) to interact with processor (12) while performing the surgical procedure.

Navigation guidewire (40) includes a sensor (not shown) that is responsive to positioning within the alternating magnetic fields generated by field generators (24), and that generates data usable to determine the position of the sensor within the magnetic fields. A coupling unit (42) is secured to the proximal end of navigation guidewire (40) and is configured to provide communication of data and other signals between console (18) and navigation guidewire (40). Coupling unit (42) may provide wired or wireless communication of data and other signals. While the position sensor is located in guidewire (40) in this example, such a position sensor may be integrated into various other kinds of instruments, such as dilation catheters, guide catheters, guide rails, suction instruments, pointer instruments, registration probes, curettes, patient trackers, and other instruments, including those described in greater detail below.

Processor (12) uses software stored in a memory of processor (12) to calibrate and operate IGS navigation system (10). Such operation includes driving field generators (24), processing data from navigation guidewire (40), processing data from operating controls (14), and driving display screen (16). Processor (12) is further operable to provide video in real time via display screen (16), showing the position of the distal end of navigation guidewire (40) in relation to a video camera image of the patient's head (H), a CT scan image of the patient's head (H), and/or a computer generated three-dimensional model of the anatomy within and adjacent to the patient's nasal cavity. Display screen (16) may display such images simultaneously and/or superimposed on each other during the surgical procedure. Such displayed images may also include graphical representations of instruments that are inserted in the patient's head (H), such as navigation guidewire (40), such that the operator may view the virtual rendering of the instrument at its actual location in real time. By way of example only, display screen (16) may provide images in accordance with at least some of the teachings of U.S. Pat. No. 10,463,242, entitled "Guidewire Navigation for Sinuplasty," issued Nov. 5, 2019, the disclosure of which is incorporated by reference herein. In the event that the operator is also using an endoscope, the endoscopic image may also be provided on display screen (16).

II. EXEMPLARY INTERFACE AND METHOD FOR VIRTUAL CAMERA NAVIGATION

It may be advantageous to provide improved interfaces and methods that allow users additional control and visual context when placing and using a virtual camera, or when user other virtual endoscopic views. A virtual camera view provides a virtual endoscopic view that is semi-statically positioned by a user in a desired location within the patient model. The virtual camera view may be repositioned and reoriented by a user, but is semi-static in the sense that it maintains a set perspective and field of view regardless of movements of others positionally tracked instruments or features.

As an example of other virtual endoscopic views, an alternate virtual endoscopic view may be provided based upon the position and orientation of a tracked surgical instrument such as a debriding tool, rather than semi-statically positioned as a virtual camera. In this manner, a surgical instrument that lacks a true endoscopic view may instead provide a virtual endoscopic view during use by navigating and displaying portions of a 3-D model based upon the tracked position of the surgical instrument. A virtual endoscopic view may be switched between semi-static virtual camera positioning and instrument determined virtual endoscopic positioning as may be desired by a user. In some implementations, an instrument determined virtual endoscopic position may be switched to a virtual camera that has already been positioned elsewhere, such that the rendered viewpoint jumps between two positions (e.g., between the already positioned virtual camera and the present position of the surgical instrument), or the virtual camera's position may be determined based upon the position of the tracked surgical instrument at the time of switching (e.g., the virtual camera's initial position may be selected by navigating the surgical instrument with the virtual endoscopic view, and then decoupling the view so that it remains in place as a virtual camera). The features described herein may be combined with a virtual camera view, another virtual endoscopic view, or both in order to provide flexible and useful virtual views.

Figure 2:
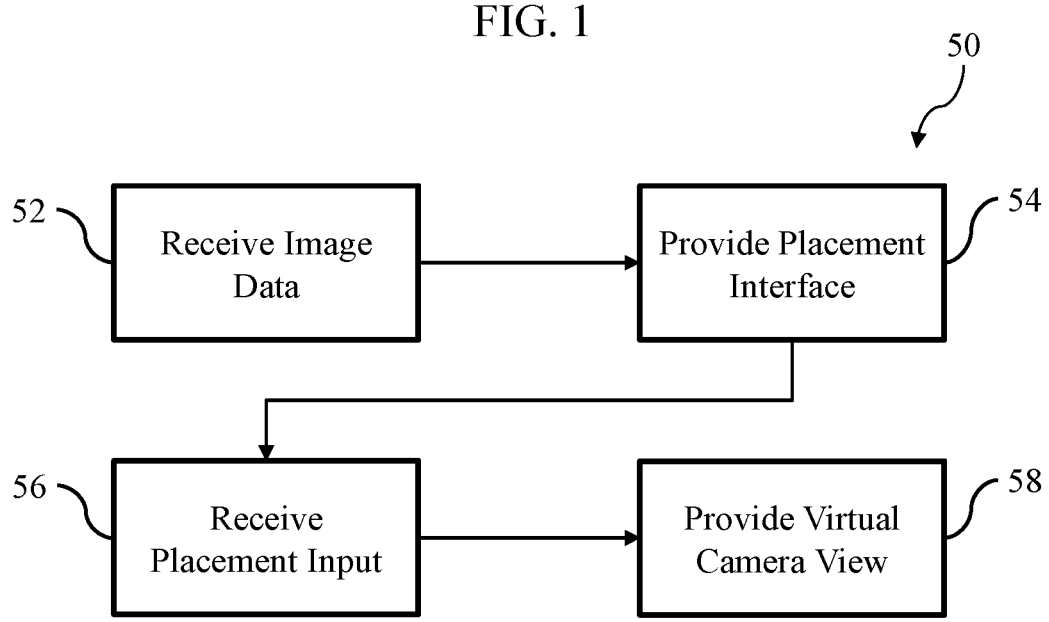
FIG. 2 shows an exemplary set of high-level steps that may be performed by or with the surgery navigation system of FIG. 1 to place a virtual camera.

FIG. 2 shows an exemplary set of high-level steps (50) that may be performed by or with a surgery navigation system such as the IGS navigation system (10) to place a virtual camera. The IGS navigation system (10) may receive (block 52) preoperative image data from one or more sources such as a hospital information system or procedure information system where such image data may be stored after it is captured. The preoperative image data may be used by the IGS navigation system (10) to provide IGS features during a surgical procedure, which may include a virtual camera positioned to provide a virtual camera view via a device such as the display (16). The IGS navigation system (10) may provide (block 54) a placement interface via the display (16) that a clinician may use to provide inputs defining the virtual camera position and orientation via an input device such as the operating controls (14). As placement inputs are received (block 56) from the clinician, the IGS navigation system (10) will update the placement interface in real-time to provide (block 58) a virtual endoscopic view or preview that may be used by the clinician to preview and provide additional placement inputs prior to a procedure, to modify placement during performance of a surgical procedure, or both.

Figure 3:
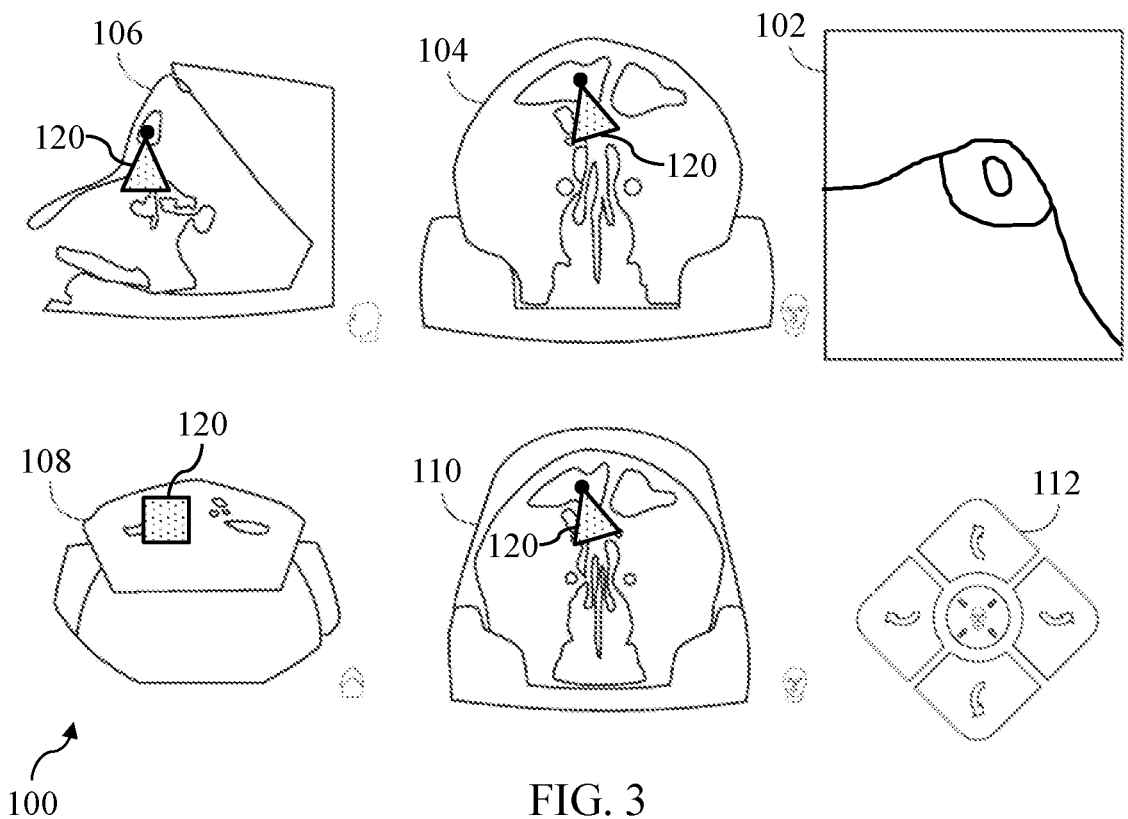
FIG. 3 shows an exemplary interface that may be displayed during image guided surgery navigation, and that includes a virtual camera interface.

FIG. 3 shows an exemplary interface (100) that may be displayed during image guided surgery navigation, and that includes a virtual camera interface. The interface (100) includes a virtual camera pane (102) that may be used to aid in configuring and placing a virtual camera; and may also display a virtual camera view after configuration. The interface (100) also includes additional views useful in IGS navigation; and is shown in FIG. 3 as including a first view (104) showing a coronal image slice of the patient, a second view (106) showing a sagittal image slice of the patient, a third view (108) showing an axial image slice of the patient, and a fourth view (110) that may show a rendered 3-D model or other view of the patient. The particular image slices or perspectives shown in each of the views may be selected by an operator of the system (10), may be updated automatically in response to movement of the navigation guidewire (40), or may be selected in other ways. The interface (100) also includes a set of controls (112) that may be interacted with in order to select images for or change perspectives of one or more of the views, or that may be to place or otherwise configure a virtual camera, for example.

A representation of a virtual camera (120) can also be seen positioned on each of the views (104, 106, 108, 110), with the black dot indicating the position of the virtual camera and the shaded triangle or square, in the case of the third view (108), indicating both the orientation and field of view of the virtual camera (120). As can be seen in FIG. 3, the virtual camera (120) is positioned within a cavity of the patient's head and is oriented towards a sinus passage which provides access to that cavity. The resulting field of view is shown in the virtual camera pane (102). While the unique perspective shown by the virtual camera pane (102) can provide valuable additional information to aid in IGS navigation, it may be limited in some cases since the virtual camera (120) functions similarly to a real camera, and so will typically be positioned in a cavity that provides a clear line of sight to the area of interest, as shown in FIG. 3.

Depending upon factors such as the type of procedure being performed or patient physiology, there may not be a readily available cavity in which the virtual camera (120) may be positioned in order to provide visual context, or the cavity may be so small or narrow that the provided visual context is not useful. This is especially true when a surgical instrument or other positionally tracked object or anatomical structure may also occupy the same narrow cavity. While the virtual camera (120) can be configured for almost any scale, and so can virtually "fit" into almost any space no matter how small, the resulting scale of images in the virtual camera pane (102) may be unhelpful or even misleading.

Figure 4:
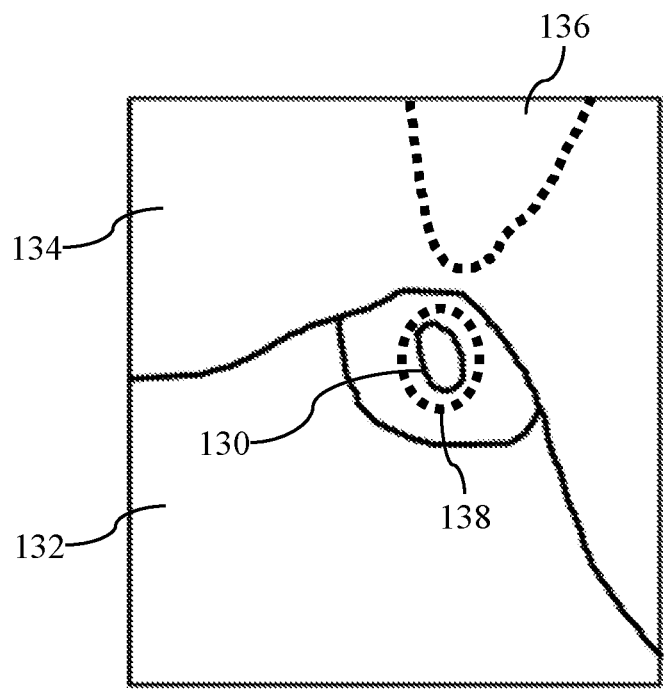
FIG. 4 shows a schematic diagram that provides an example of visualization of a surgical site with a virtual camera.

As an example, FIG. 4 shows a schematic diagram that provides an example of visualization of a surgical site with a virtual camera. An opening (130) to an anatomical passage (e.g., a sinus passage, Eustachian tube, etc.) can be seen, and the wall (138) of the anatomical passage is roughly represented by a dotted oval surrounding the opening (130). Other background anatomical surfaces are also shown (132, 134) surrounding the opening (130). In a scenario where a procedure is being performed within the anatomical passage (e.g., cutting or debriding of a fibroid mass on the wall (138)), the present position of the virtual camera (120) may not be ideal as the view is largely occupied by the background anatomy (132, 134) which may be of little importance for the procedure. Further, the opening (130) may be narrowed than the circumference of the wall (138), and so the tissue of the opening (130) itself may wholly or partially obscure the procedure site.

The present position of the virtual camera (120) is also limited in the context it can provide relative to other critical anatomical structures. For example, FIG. 4 also includes a dotted line indicating a critical anatomical structure such as an ocular cavity (136) which is proximate to the surgical site but is not visible due to intervening structures such as the background tissue (134). A debriding procedure on the wall (138) may involve cutting or removing tissue that is proximate to optical nerves, blood vessels, or other delicate anatomy within the ocular cavity (136), and so an IGS navigation view that could provide some indication of proximity to such critical structures during the procedure may be advantageous. While moving the virtual camera (120) from the position of FIG. 4 may provide some advantage, it is still limited due to issues of scale and intervening tissue or instruments.

Figure 5A:
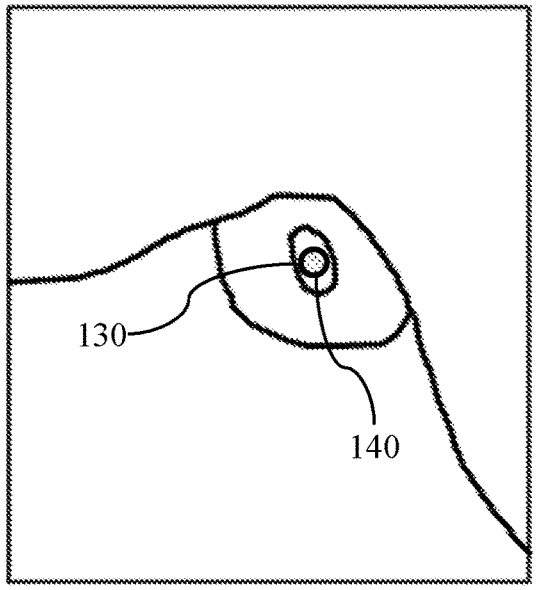
FIG. 5A shows an exemplary virtual camera view that may be displayed via the interface of FIG. 3.

These limitations of the virtual camera view may be addressed by providing a virtual camera system and interface that allows for selective control over the rendering of anatomical structures within the virtual camera pane (102). FIGS. 5A-5D further illustrate the problem associated with virtual camera positioning, as well as the advantage provided by selective rendering. FIG. 5A shows a view similar to that shown in FIG. 4, but also including an instrument tip (140) that is visible within the opening (130). The instrument tip (140) may be representative of a distal tip of a positionally tracked surgical instrument (e.g., a tissue debrider) that has been navigated to the surgical site for use in the procedure. The view of FIG. 5A may be useful in initially navigating and positioning the instrument tip (140); but provides little visual context that would be useful during a tissue debriding procedure or other procedure within the anatomical passageway.

Figure 5B:
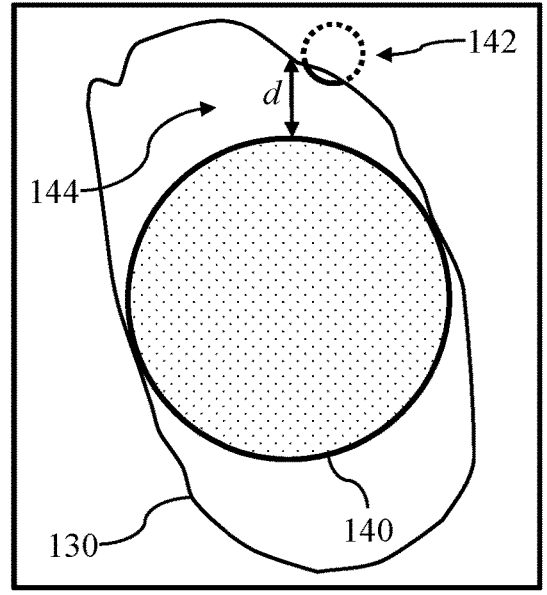
FIG. 5B shows a magnified portion of the virtual camera view of FIG. 5A.

FIG. 5B shows a magnified view of the opening (130) such as might be achieved by repositioning the virtual camera (120) to be closer to the opening (130). In this view, it can be seen that the instrument tip (140) occupies the majority of the view, and that the instrument tip (140) and the tissue surrounding the opening (130) still partially obstruct the interior of the anatomical passage. A surgical site (142) (e.g., a fibroid mass on the wall (138) of the passage) is partially visible, but still largely obstructed such that it will not remain visible throughout the surgical procedure. The ocular cavity (136) that is proximate to the surgical site (142) is not visible in the magnified view. While the virtual camera (120) could be positioned within the anatomical passage (144) itself, the distance d between the instrument tip (140) and the wall (138) of the passage (144) is narrow enough that the scale of the resulting view would not provide helpful visual context. As an example, a virtual view of the surgical site (142) from within the passage (144) might show only a portion of the surgical site (142) (e.g., the entirety of the view may be focused on a small portion of a fibroid mass) or might be entirely obstructed by the instrument tip (140) (e.g., especially true when the instrument tip (140) is in physical contact with the surgical site (142)).

Figure 5C:
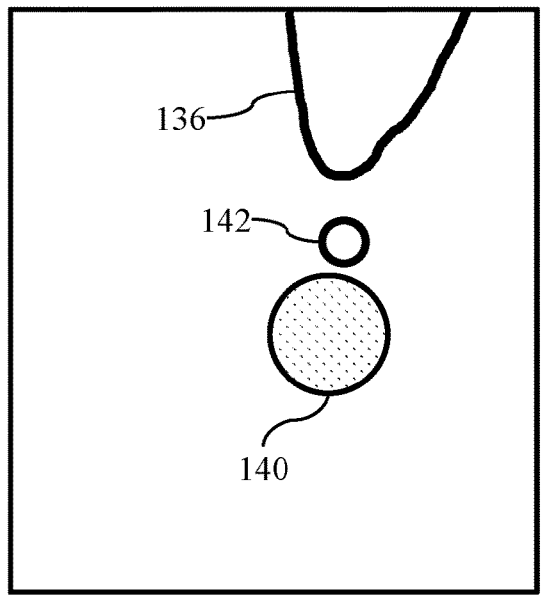
FIG. 5C shows an exemplary modified virtual camera view that may be displayed via the interface of FIG. 3.
Figure 5D:
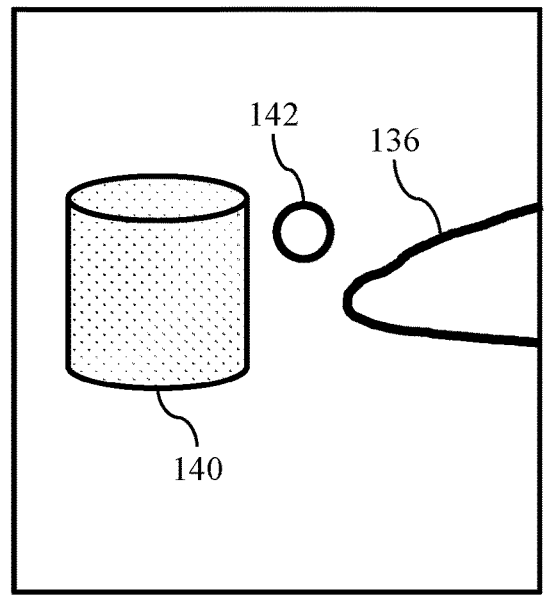
FIG. 5D shows the modified virtual camera view of FIG. 5D from a different perspective.

An IGS navigation system configured to provide virtual camera placement and viewing with selective rendering of anatomy addresses these limitations by omitting anatomical structures that are determined to be irrelevant to the present procedure, or that are otherwise determined to be undesirable for inclusion in the rendered virtual camera view. FIG. 5C shows an exemplary modified virtual camera view, with virtual camera placement similar to that of FIGS. 5A and 5B. The instrument tip (140) is still visible positioned proximately to the surgical site (142). However, the opening (130) and background anatomy (132, 134), as well as other intervening tissues or structures have been omitted so that the ocular cavity (136) is also visible. With such a view, a surgeon may visually confirm the position of the instrument tip (140) relative to the surgical site; and may also visually confirm the position of the instrument tip (140) relative to the nearby ocular cavity (136) or other critical structure. FIG. 5D shows the modified virtual camera view of FIG. 5D from a different perspective, such as may be shown after the virtual camera (120) is repositioned. An IGS navigation system configured for such selective rendering, as will be described in more detail below, allows for additional placement positions and visualization capabilities beyond that of a basic virtual camera.

Figure 6:
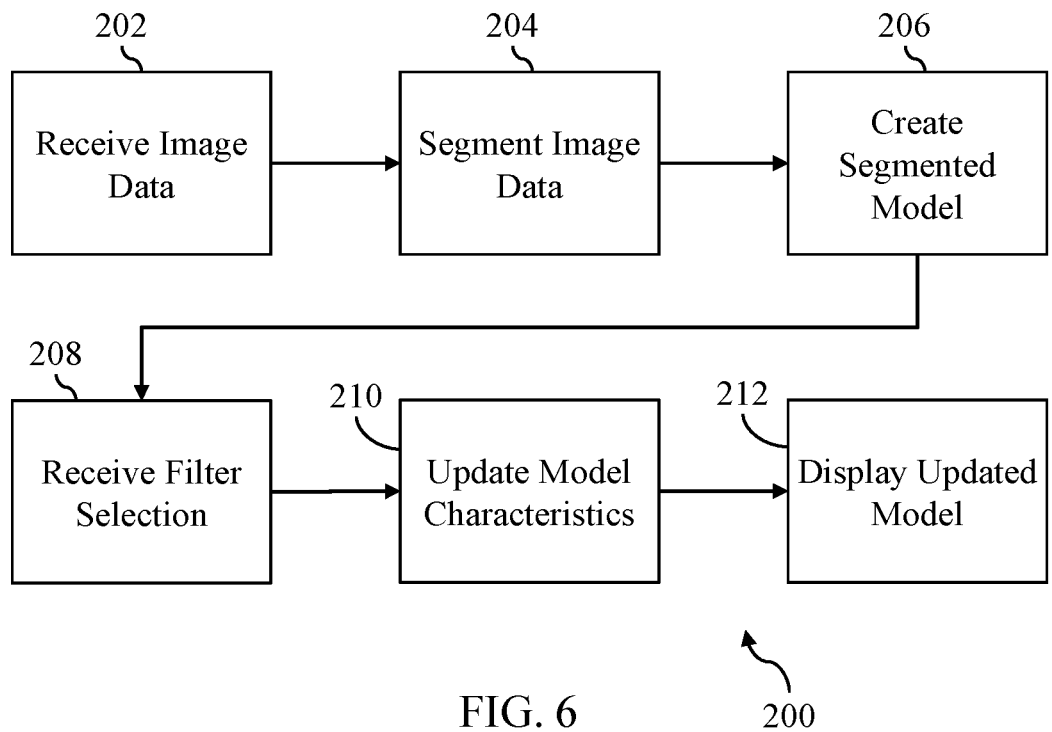
FIG. 6 shows an exemplary set of high-level steps that may be performed by or with the surgery navigation system of FIG. 1 to modify a virtual camera view.

A system such as the IGS navigation system (10) may be configured to provide virtual camera placement and viewing with selective rendering, with one or more processors such as the processor (12) being configured to selectively render and display the virtual camera view via a display such as the display screen (16). FIG. 6 shows an exemplary set of high-level steps (200) that may be performed to modify a virtual camera view for selective rendering. Image data may be received (block 202) as a set of preoperative images (e.g., image slices from an MM scan) and may be combined and segmented (block 204) in order to produce (block 206) a segmented 3-D model of the patient anatomy. Segmentation (block 204) may include creating a voxel model of the patient anatomy, associating specific regions of a model with certain patient anatomy, or both. As an example, a set of MRI image slices from several views (axial, coronal, sagittal) may be combined such that the intersecting planes produce voxels that are spatially associated with each other, and that may be associated with metadata indicating signal intensity, tissue type, or other attributes of the voxel and underlying image slice data. Further segmentation of a voxel model or other patient anatomy model may include identifying and categorizing discrete anatomical structures. Identification of anatomical structures may be performed manually (e.g., by a user selecting a region of voxels or other 3-D data and labeling them as an ocular cavity) or automatically (e.g., by an automated process that searches for voxels or other 3-D data associated with certain tissue types in a particular shape or having a particular spatial relationship to other structures and labeling them as an ocular cavity), as will be apparent to those of ordinary skill in the art in light of this disclosure. The model created (block 206) from segmentation may be stored and used for IGS navigation, including placement of virtual cameras, rotation and manipulation within 3-D space, and stepping through image slices or voxel layers to produce cross sectional views, for example.

The IGS navigation system (10) may then receive (block 208) a filter selection that identifies one or more segments (e.g., voxels, segmented and identified anatomy, or other parameters defining a 3-D region within a model) that are to be filtered out of the final rendering of the model when used for providing a virtual camera view. Filtered segments may be identified in a variety of ways such as a whitelist (e.g., all segments not listed are filtered), a blacklist (e.g., only listed segments are filtered), or other types or combinations of filtering, as will be described in more detail below. Filter selections may be made manually (e.g., by a user selecting segments that are to be included or excluded from the rendering) or automatically, with automatic filtering selections being determined by factors such as the type of procedure (e.g., when IGS navigation begins for a particular type of procedure, filtering selections may be automatically made based on that procedure type) or the placement and orientation of the virtual camera (e.g., filtering selections could include all segments within a sphere of a certain circumference centered on the virtual camera, or could include all segments within a cone or cuboid originating from the virtual camera).

The system may then update (block 210) the model characteristics based upon the filter selection in order to determine which segments should be included in the final rendering, and which segments should be filtered from the final rendering. The updated and filtered model may then be displayed (block 212) in one or more views such as the virtual camera pane (102) or the fourth view (110) and used to aid in navigation and performance of a procedure.

Figure 7:
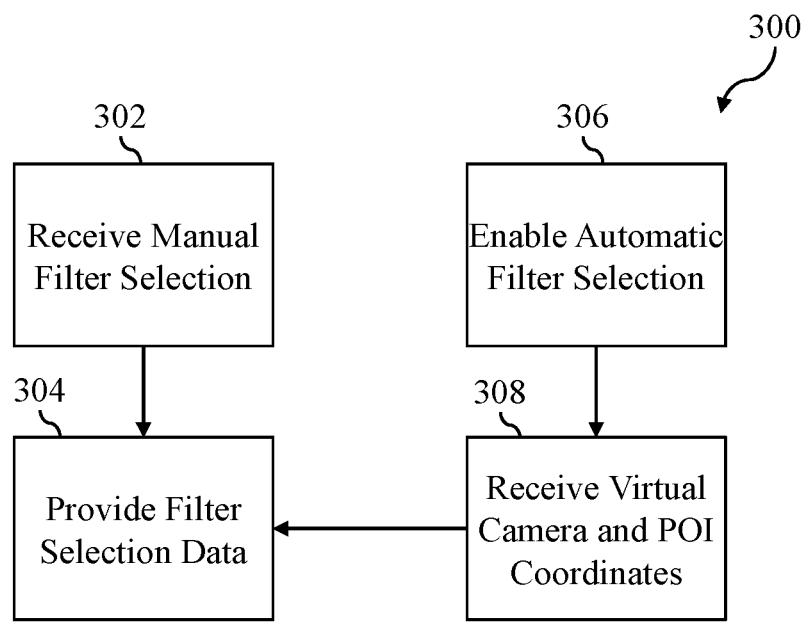
FIG. 7 shows an exemplary set of steps that may be performed to determine filter inputs for a virtual camera view.

As an example of steps that may be performed when selecting segments (e.g., voxels, identified anatomy, or other 3-D regions) for filtering, FIG. 7 shows an exemplary set of steps (300) that may be performed to determine filter inputs for a virtual camera view. Manual filtering selections may be received (block 302) prior to a procedure or during a procedure. Prior to a procedure, a surgeon or other user may review a 3-D model of the patient anatomy and, using a mouse, keyboard, or other input device, navigate the model and select segments for inclusion or exclusion from the virtual camera view. Manual selections may be made by interacting with the model itself (e.g., clicking on the model to remove the entire clicked segment) or by making selections from a list or other set of data (e.g., clicking on a procedure type, a group of anatomy, or a particular anatomical structure). Selection may be made during a procedure by clicking on or, in the case of a touchscreen display, touching a displayed segment to remove it from the rendered virtual camera view, for example.

As an alternative or addition to manual filter selections (block 302), the system may also be enabled (block 306) to perform one or more types of automatic selection (block 306). As has been described, automatic selection may be performed based upon a procedure type or description. As an example, where a procedure is associated with debriding a fibroid on the wall (138) of an anatomical passage as in FIG. 5A, the system may automatically filter out unrelated segments in order to provide a view such as that shown in FIG. 5C. Such automatic filtering may be based on the procedure type and other factors, such as the particular surgeon associated with performing the procedure, such that each surgeon may pre-configure their own preferences for automatic filtering for that type of procedure. Other types of pre-determined or static automatic filter selections may be based on information such as the instrument type being used in a procedure, patient specific information describing unique physiology or risks, or pre-determined locations of surgical instruments or other tracked objects during the procedure (e.g., a set of automatically filtered segments may change or be updated as the instrument tip (140) reaches various positions or milestones during performance of the procedure). Once received or determined, the manual filter selections may be provided (block 304) to a process or processor associated with rendering the model.

Automatic filter selection (block 306) may also be performed based on dynamic factors that arise during a procedure. This could include dynamically updating the filter selections based on data such as the position and orientation of the virtual camera (120), the position and orientation of the instrument tip (140), and the position and orientation of patient anatomy at or near the surgical site (142), for example. One example of dynamic filtering includes receiving (block 308) coordinates describing the position and orientation of the virtual camera, as well as the positions of one or more other points of interest (POI) such as the instrument tip (140), a nearby critical anatomy such as the ocular cavity (136), the surgical site (142), or other segments, regions, areas, or objects that may be relevant to the current procedure. The received (block 308) virtual camera and POI coordinates may then be used to determine (block 310) one or more dynamic filtering selections that are configured to provide better visibility between and around the POIs and the virtual camera. As an example, this could include filtering out intervening segments that are present along the optical axis of the virtual camera and one or more POIs, so that the POIs are visible to the virtual camera regardless of its placement. This could also include filtering out segments that are within a configured distance of the instrument tip (140) (e.g., a sphere of several centimeters diameter) to provide clear lines of sight to the instrument tip (140) when the virtual camera is positioned nearby. As with prior examples, once the parameters for dynamic or other automatic filtering are determined (block 310), they can be provided (block 304) to a process or processor associated with rendering the model.

Dynamic filtering could be combined with other filtering selections to provide even more control over filtering, and individual filters could be given a priority or hierarchy to determine which filter controls. Building on a previous example, automatic filtering of intervening segments could be combined with a whitelist of segments that are never filtered, even when they are positioned within the field of view of the virtual camera and intervene or block visibility to a POI. With reference to FIGS. 5C and 5D, this could allow the ocular cavity (136) and the surgical site (142) to be whitelisted so that they are always rendered. The virtual camera may then be positioned anywhere in the 3-D space of the model and oriented towards the surgical site (142) as a POI. All intervening segments would be automatically filtered from the rendering providing a clear line of sight to the surgical site (142) and the instrument tip (140) via the virtual camera view. If the virtual camera were to travel in a circle while staying oriented on the surgical site (142), the filtered segments could be dynamically updated and either filtered or rendered to always provide a clear line of sight to the surgical site (142), except in the case of the ocular cavity (136) which would always be visible, even when fully or partially blocking view of the surgical site (142), due to being configured on the whitelist of rendered segments.

Varying configurations for dynamic filtering can provide a high level of control and visibility over the virtual camera view, and could allow for the virtual camera to orbit the POI along varying axes to gain visual and spatial perspective of the relationship between the instrument tip (140) and various POI. Such movements of the virtual camera could be performed with the set of controls (112), or could be configured to be performed automatically in response to various one-touch controls (e.g., a one-touch button that causes the virtual camera to orbit around the POI along the X-axis with dynamic filtering of the rendered virtual camera view). Varying preconfigured one-touch movements of the virtual camera could be triggered from the interface (100), could be triggered by voice inputs, or could be triggered by controls positioned on a surgical instrument being used during the procedure, as may be advantageously implemented in varying applications.

Figure 8:
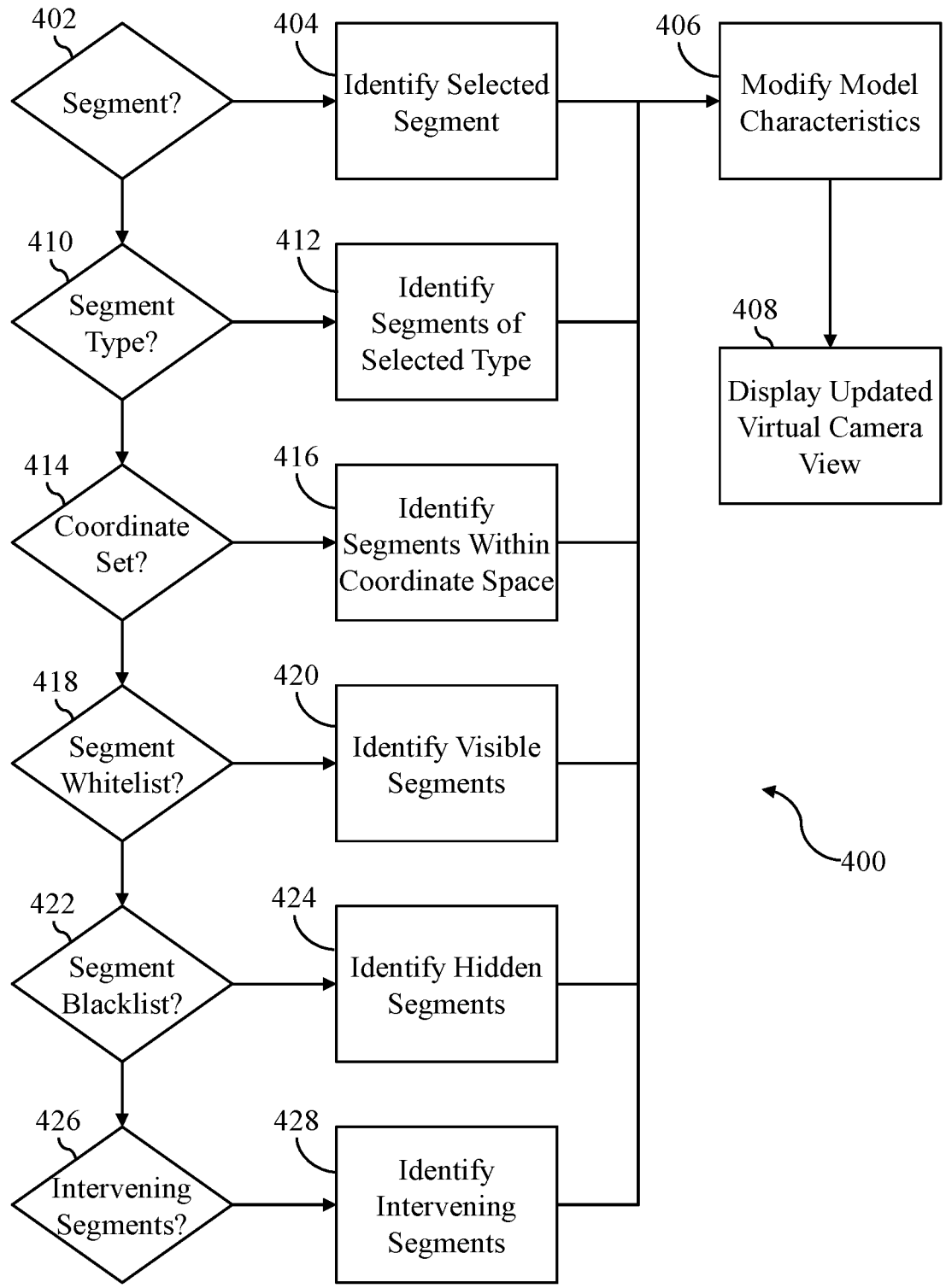
FIG. 8 shows an exemplary set of steps that may be performed to apply filter inputs to a virtual camera view.

FIG. 8 shows an exemplary set of steps (400) that may be performed to update a patient model based upon one or more filter selections that are manually configured or automatically determined. When a set of filter selections are available, the system may determine one or more segments (e.g., voxels, segmented and identified anatomy, or other parameters defining a 3-D region within a model) that are impacted by the filter selections, and then will modify (block 406) the model characteristics of the patient model and display (block 408) an updated virtual camera view based on the modified patient model. This may be performed prior to the procedure or during the procedure, in the case of manual selections made during the procedure or automatic selections that are applied or dynamically determined during the procedure.

Whether manual or automatic, filter selections may be configured and stored on the system as varying types. When the system applies the filter selections, the segments that are identified for inclusion or exclusion may be determined by the filter type. As an example, some filter selections may directly identify segments (block 402) as voxel sets, identified anatomy, or other regions. Identification (block 404) of such segments may be performed by identifying them within the model based upon the selection (e.g., by a range of voxels that define a region, by a unique identifier associated with an identified anatomy), and determining whether the filter selection indicates that the identified segments should be included and visible in the model, or excluded and hidden from the model when it is displayed (block 408).

Some filter selections may indicate types of segments (block 410) rather than particular segments. Identification (block 412) of segments based upon a selected type may include searching the model and identifying all segments that match the specified type, and then determined whether the identified segments should be visible or hidden in the displayed (block 408) view. As an example, a type selection might specify voxels that are associated with data indicating a certain tissue type or density such as "bone" or "soft tissue", and filtering upon such a selection may result in a set of voxels or segments associated with soft tissue being hidden, or a set of voxels or segments associated with bone being visible. As another example, a type selection might specify segments that are associated with a certain procedure (e.g., sinus fibroid removal). Filtering based upon a procedure type may result in a set of segments associated with that procedure being visible, while other segments that are not relevant to the procedure or might obstruct virtual camera views of the procedure being hidden. Another type selection may identify a set of anatomy by a grouping such as an organ system (e.g., circulatory system), such that filtering selections might cause all segmented and identified anatomy of certain types, groups, or organ systems to be visible or hidden.

Some filter selections may provide coordinates (block 414) that are not specific segmented anatomy, but that are associated with a coordinate system in which the patient model exists. This may include a selection of a single coordinate by a mouse, a click-and-drag selection of a two-dimensional array of coordinates by a mouse, or another set of coordinates defining a region within the 3-D coordinate system (e.g., a 3-D cuboid, a sphere, or an arbitrarily defined shape). Identification (block 416) of affected segments may include relating the coordinate set to the coordinate system of the patient model and then identifying any segments that touch on or are contained by (e.g., either entirely or partially) the coordinate set. In this manner, a mouse click associated with a single coordinate may only cause a single segmented anatomy to disappear, while clicking a mouse and then dragging to expand a 3-D sphere or cuboid from the initial point may cause a plurality of segments to disappear. Pre-configure coordinate sets may also be used to define 3-D regions or segments for inclusion or exclusion from the displayed (block 408) view.

Some filter selections may be in the form of a segment whitelist (block 418) or segment blacklist (block 422), as has been described. Identification (block 420) of whitelisted segments may include associating the listed segments as being visible and hiding all other segments, while identification (block 424) of blacklisted segments may include associating the listed segments as being hidden; and making all other segments visible. Filter selections based upon intervening segments (block 426) have also been described, and may include identifying (block 428) within the coordinate system any segments that fall between two or more points within the system (e.g., between a first coordinate associated with the virtual camera and a second coordinate associated with a point of interest or tracked surgical instrument). Identified (block 428) intervening segments may then be made visible or hidden, depending upon the filter selection.

As has been described, differing types of filter selections may be combined and given priority relative to each other, such as a whitelisted set of segments that are always visible even when they are determined to be intervening (block 428) segments that obstruct a point of interest. As another example, a whitelisted set of segments may always remain visible, even when they fall within a coordinate space defined by mouse selections or other inputs that cause surrounding segments to be excluded from the displayed (block 408) rendering. As will be apparent, other combinations and priorities of filter selections exist beyond those described.

When modifying (block 406) the characteristics of the patient model based upon filtering selections, varying types of visually distinct characteristics may be used beyond simply making the segments hidden or visible. As an example, this could include highlighting a segment, making a segment semi-transparent, displaying a segment with dynamic transparency so that it fades in and out of visibility, configuring a segment to project a field of light or a particle cloud within the 3-D space of the model such that the projected light or projected particles might be visible to the virtual camera even when the originating segment is obstructed by other anatomy, or other visual characteristics.

Variations on the systems, methods, and interfaces described above exist and will be apparent to one of ordinary skill in the art in light of this disclosure. For example, while some of the above discussion has described the first point as being the virtual camera's location, it should be understood that in some implementations the first point may be the virtual camera's orientation. This may be advantageous where a clinician has determined a position within the surgical area that is of interest and wishes to select that as the point of orientation (i.e., the second point), then preview a number of camera positions (e.g., the first point) using the real-time virtual endoscopic preview and relational flythrough before making a selection. Choosing the virtual camera's location as the first point may be advantageous where a clinician may use their experience to first determine the best location for the virtual camera, and then may use the real-time virtual endoscopic preview and relational flythrough to choose a point of the surgical area that they would like to focus the virtual camera upon.

III. EXEMPLARY COMBINATIONS

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

An image guided surgery system comprising: (a) a display; (b) a set of preoperative images associated with a patient; (c) a tracked surgical instrument configured to produce a set of instrument location information that is associated with a coordinate system; (d) a processor configured to: (i) segment the set of preoperative images to produce a patient model and associate the patient model with the coordinate system, wherein the patient model comprises a three-dimensional model of the patient's anatomy comprised of a plurality of segments, (ii) categorize the plurality of segments into two or more segment groups based upon a filter selection, wherein each of the two or more segment groups is associated with a different visual characteristic, (iii) render a modified patient model based on the different visual characteristic of each of the two or more segment groups, (iv) receive a set of virtual camera configurations that define a position and an orientation of a virtual camera within the coordinate system, and (v) cause the display to show a virtual camera view of the modified patient model based on the set of virtual camera configurations and the set of instrument location information.

Example 2

The system of example 1, wherein: (i) a first visual characteristic associated with a first group of the two or more segment groups is configured to cause segments in the first group to be included in the modified patient model, and (ii) a second visual characteristic associated with a second group of the two or more segment groups is configured to cause segments in the second group to be excluded from the modified patient model.

Example 3

The system of example 2, wherein the filter selection comprises an identification of a segment that is to be included in the second group, and wherein the processor is further configured to: (i) receive the filter selection prior to a surgical procedure associated with the patient, and (ii) receive the filter selection via a user input device of the image guided surgery system during the surgical procedure associated with the patient.

Example 4

The system of any one or more of examples 2 through 3, wherein the filter selection comprises a procedure type, and wherein the processor is further configured to identify the second group in the plurality of segments based on the procedure type being associated with those segments.

Example 5

The system of any one or more of examples 2 through 4, wherein the filter selection comprises a tissue type, and wherein the processor is further configured to identify the second group in the plurality of segments based on the tissue type matching a tissue type characteristic associated with each of the plurality of segments.

Example 6

The system of any one or more of examples 1 through 5, wherein the processor is further configured to determine the filter selection by: (i) identifying a set of proximate segments from the plurality of segments that are within a configured distance of the position of the virtual camera within the coordinate system, and (ii) associating the set of proximate segments with a first group of the two or more segment groups, wherein the different visual characteristic of the first group is configured to cause segments in the first group to be excluded from the modified patient model.

Example 7

The system of any one or more of examples 1 through 6, wherein the processor is further configured to determine the filter selection by: (i) identifying a set of proximate segments from the plurality of segments that are within a configured distance of the position of the tracked surgical instrument within the coordinate system, and (ii) associating the set of proximate segments with a first group of the two or more segment groups, wherein the different visual characteristic of the first group is configured to cause segments in the first group to be excluded from the modified patient model.

Example 8

The system of any one or more of examples 1 through 7, wherein the processor is further configured to determine the filter selection by: (i) identifying a set of intervening segments from the plurality of segments that are positioned along an axis between the virtual camera and a position in the coordinate system that is associated with a point of interest, and (ii) associating the set of intervening segments with a first group of the two or more segment groups, wherein the different visual characteristic of the first group is configured to cause segments in the first group to be excluded from the modified patient model.

Example 9

The system of example 8, wherein the point of interest comprises a surgical site associated with a procedure being performed on the patient.

Example 10

The system of example 9, wherein the filter selection further comprises a segment whitelist that describes one or more whitelisted segments of the plurality of segments, and wherein the processor is further configured to prevent the whitelisted segments from being associated with the first group and excluded from the modified patient model.

Example 11

The system of example 10, wherein the processor is further configured to: (i) receive a user input configured to cause a one-touch virtual camera movement, (ii) determine a path within the coordinate system based on the user input, (iii) move the virtual camera from an origin point along the path until the virtual camera returns to the origin point while maintaining the virtual camera's orientation on the surgical site, and (iv) update the patient model based on changes in the set of intervening segments during movement of the virtual camera along the path.

Example 12

The system of any one or more of examples 1 through 11, wherein the plurality of segments comprises one or more of:

(i) voxels, (ii) sets of adjacent voxels, or (iii) anatomical structures identified based upon their shape and location in the patient model.

Example 13

The system of any one or more of examples 1 through 12, wherein each different visual characteristic is selected from a set of visual characteristics comprising: (i) opaque, (ii) partially translucent (iii) transparent, and (iv) gradual increase and reduction of opacity.

Example 14

A method for selectively controlling segments shown by a virtual camera comprising: (a) with a processor, segmenting a set of preoperative images to produce a patient model and associating the patient model with a coordinate system, wherein the patient model comprises a three-dimensional model of a patient's anatomy comprised of a plurality of segments; (b) categorizing the plurality of segments into two or more segment groups based upon a filter selection, wherein each of the two or more segment groups is associated with a different visual characteristic; (c) rendering a modified patient model based on the different visual characteristic of each of the two or more segment groups; (d) receiving a set of virtual camera configurations that define a position and an orientation of the virtual camera within the coordinate system; (e) receiving a set of instrument location information that indicates a tracked surgical instrument within the coordinate system; and (e) causing a display to show a virtual camera view of the modified patient model based on the set of virtual camera configurations and the set of instrument location information.

Example 15

The method of example 14, further comprising receiving the filter selection prior to a surgical procedure associated with the patient, wherein: (i) a first visual characteristic associated with a first group of the two or more segment groups is configured to cause segments in the first group to be included in the modified patient model, (ii) a second visual characteristic associated with a second group of the two or more segment groups is configured to cause segments in the second group to be excluded from the modified patient model, and (iii) the filter selection comprises an identification of a segment of the plurality of segments to be included in the second group of the two or more segment groups.

Example 16

The method of any one or more of examples 14 through 15, further comprising: (a) determining a procedure type based upon the filter selection; and (b) categorizing the plurality of segments into an included segment group and an excluded segment group based upon the procedure type.

Example 17

The method of any one or more of examples 14 through 16, further comprising: (a) determining a filtered tissue type based upon the filter selection; and (b) categorizing the plurality of segments into an included segment group and an excluded segment group based upon the filtered tissue type matching a tissue type characteristic associated with each of the plurality of segments.

Example 18

The method of any one or more of examples 14 through 17, further comprising determining the filter selection by: (i) identifying a set of proximate segments from the plurality of segments that are within a configured distance of the position of the virtual camera within the coordinate system, and (ii) associating the set of proximate segments with a first group of the two or more segment groups, wherein the different visual characteristic of the first group is configured to cause segments in the first group to be excluded from the modified patient model.

Example 19

The method of any one or more of examples 14 through 18, further comprising determining the filter selection by: (i) identifying a set of intervening segments from the plurality of segments that are positioned along an axis between the virtual camera and a surgical site in the coordinate system, and (ii) associating the set of intervening segments with a first group of the two or more segment groups, wherein the different visual characteristic of the first group is configured to cause segments in the first group to be excluded from the modified patient model.

Example 20

An image guided surgery system comprising one or more processors configured to: (i) maintain a coordinate system, (ii) segment a set of preoperative images to produce a patient model and associate the patient model with the coordinate system, wherein the patient model comprises a three-dimensional model of the patient's anatomy comprised of a plurality of segments, (iii) categorize the plurality of segments into two or more segment groups based upon a filter selection, wherein each of the two or more segment groups is associated with a different visual characteristic, (iv) render a modified patient model based on the different visual characteristic of each of the two or more segment groups, (v) receive a set of virtual camera configurations that defines a position and an orientation of a virtual camera within the coordinate system, (vi) receive a set of instrument location information that indicates a tracked surgical instrument within the coordinate system, (vii) cause the display to show a virtual camera view of the modified patient model based on the set of virtual camera configurations and the set of instrument location information.

IV. MISCELLANEOUS

It should be understood that any of the examples described herein may include various other features in addition to or in lieu of those described above. By way of example only, any of the examples described herein may also include one or more of the various features disclosed in any of the various references that are incorporated by reference herein.

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those skilled in the art in view of the teachings herein. Such modifications and variations are intended to be included within the scope of the claims.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices disclosed herein can be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, versions of the device may be disassembled, and any number of the particular pieces or parts of the device may be selectively replaced or removed in any combination. Upon cleaning and/or replacement of particular parts, versions of the device may be reassembled for subsequent use either at a reconditioning facility, or by a surgical team immediately prior to a surgical procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be processed before surgery. First, a new or used instrument may be obtained and if necessary cleaned. The instrument may then be sterilized. In one sterilization technique, the instrument is placed in a closed and sealed container, such as a plastic or TYVEK bag. The container and instrument may then be placed in a field of radiation that can penetrate the container, such as gamma radiation, x-rays, or high-energy electrons. The radiation may kill bacteria on the instrument and in the container. The sterilized instrument may then be stored in the sterile container. The sealed container may keep the instrument sterile until it is opened in a surgical facility. A device may also be sterilized using any other technique known in the art, including but not limited to beta or gamma radiation, ethylene oxide, or steam.

Having shown and described various versions of the present invention, further adaptations of the methods and systems described herein may be accomplished by appropriate modifications by one skilled in the art without departing from the scope of the present invention. Several of such potential modifications have been mentioned, and others will be apparent to those skilled in the art. For instance, the examples, versions, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:
1. An image guided surgery system comprising:
   (a) a display;
   (b) a set of preoperative images associated with a patient;
   (c) a tracked surgical instrument configured to produce a set of instrument location information that is associated with a coordinate system; and
   (d) a processor configured to:
      (i) segment the set of preoperative images to produce a patient model and associate the patient model with the coordinate system, wherein the patient model comprises a three-dimensional model of the patient's anatomy comprised of a plurality of segments,
      (ii) identify, for each segment of the plurality of segments, an anatomical structure of the patient corresponding to each segment,
      (iii) determine a filter selection indicative of a surgical procedure to be performed on the patient using the image guided surgery system,
      (iv) categorize each segment of the plurality of segments into two or more segment groups based upon the filter selection indicative of the surgical procedure and on the anatomical structure corresponding to the respective segment, wherein each of the two or more segment groups is associated with a different visual characteristic,
      (v) render a modified patient model based on the different visual characteristic of each of the two or more segment groups,
      (vi) receive a set of virtual camera configurations that define a position and an orientation of a virtual camera within the coordinate system, and
      (vii) cause the display to show a virtual camera view of the modified patient model based on the set of virtual camera configurations and the set of instrument location information.

2. The system of claim 1, wherein:
   (i) a first visual characteristic associated with a first group of the two or more segment groups is configured to cause segments in the first group to be included in the modified patient model, and
   (ii) a second visual characteristic associated with a second group of the two or more segment groups is configured to cause segments in the second group to be excluded from the modified patient model.

3. The system of claim 2, wherein the filter selection further comprises an identification of a segment that is to be included in the second group, and wherein the processor is further configured to:
   (i) receive the filter selection prior to a surgical procedure associated with the patient, and
   (ii) receive the filter selection via a user input device of the image guided surgery system during the surgical procedure associated with the patient.

4. The system of claim 2, wherein the filter selection further comprises a tissue type, and wherein the processor is further configured to identify the second group in the plurality of segments based on the tissue type matching a tissue type characteristic associated with each of the plurality of segments.

5. The system of claim 1, wherein the processor is further configured to determine the filter selection by:
   (i) identifying a set of proximate segments from the plurality of segments that are within a configured distance of the position of the virtual camera within the coordinate system, and (ii) associating the set of proximate segments with a first group of the two or more segment groups, wherein the different visual characteristic of the first group is configured to cause segments in the first group to be excluded from the modified patient model.

6. The system of claim 1, wherein the processor is further configured to determine the filter selection by:
(i) identifying a set of proximate segments from the plurality of segments that are within a configured distance of the position of the tracked surgical instrument within the coordinate system, and
(ii) associating the set of proximate segments with a first group of the two or more segment groups, wherein the different visual characteristic of the first group is configured to cause segments in the first group to be excluded from the modified patient model.

7. The system of claim 1, wherein the processor is further configured to determine the filter selection by:
(i) identifying a set of intervening segments from the plurality of segments that are positioned along an axis between the virtual camera and a position in the coordinate system that is associated with a point of interest, and
(ii) associating the set of intervening segments with a first group of the two or more segment groups, wherein the different visual characteristic of the first group is configured to cause segments in the first group to be excluded from the modified patient model.

8. The system of claim 7, wherein the point of interest comprises a surgical site associated with a procedure being performed on the patient.

9. The system of claim 8, wherein the filter selection further comprises a segment whitelist that describes one or more whitelisted segments of the plurality of segments, and wherein the processor is further configured to prevent the whitelisted segments from being associated with the first group and excluded from the modified patient model.

10. The system of claim 9, wherein the processor is further configured to:
(i) receive a user input configured to cause a one-touch virtual camera movement,
(ii) determine a path within the coordinate system based on the user input,
(iii) move the virtual camera from an origin point along the path until the virtual camera returns to the origin point while maintaining the virtual camera's orientation on the surgical site, and
(iv) update the patient model based on changes in the set of intervening segments during movement of the virtual camera along the path.

11. The system of claim 1, wherein the plurality of segments comprises one or more of:
(i) voxels,
(ii) sets of adjacent voxels, or
(iii) anatomical structures identified based upon their shape and location in the patient model.

12. The system of claim 1, wherein each different visual characteristic is selected from a set of visual characteristics comprising:
(i) opaque,
(ii) partially translucent
(iii) transparent, and
(iv) gradual increase and reduction of opacity.

13. A method for selectively controlling segments shown by a virtual camera comprising:
with a processor,
(a) segmenting a set of preoperative images to produce a patient model and associating the patient model with a coordinate system, wherein the patient model comprises a three-dimensional model of a patient's anatomy comprised of a plurality of segments;
(b) identify, for each segment of the plurality of segments, an anatomical structure of the patient corresponding to each segment,
(c) determine a filter selection indicative of a surgical procedure to be performed on the patient using the image guided surgery system,
(d) categorizing each segment of the plurality of segments into two or more segment groups based upon the filter selection indicative of the surgical procedure and on the anatomical structure corresponding to the respective segment, wherein each of the two or more segment groups is associated with a different visual characteristic;
(e) rendering a modified patient model based on the different visual characteristic of each of the two or more segment groups;
(f) receiving a set of virtual camera configurations that define a position and an orientation of the virtual camera within the coordinate system;
(g) receiving a set of instrument location information that indicates a tracked surgical instrument within the coordinate system; and
(h) causing a display to show a virtual camera view of the modified patient model based on the set of virtual camera configurations and the set of instrument location information.

14. The method of claim 13, further comprising receiving the filter selection prior to a surgical procedure associated with the patient, wherein:
(i) a first visual characteristic associated with a first group of the two or more segment groups is configured to cause segments in the first group to be included in the modified patient model,
(ii) a second visual characteristic associated with a second group of the two or more segment groups is configured to cause segments in the second group to be excluded from the modified patient model, and
(iii) the filter selection further comprises an identification of a segment of the plurality of segments to be included in the second group of the two or more segment groups.

15. The method of claim 13, further comprising:
(a) determining a filtered tissue type based upon the filter selection; and
(b) categorizing the plurality of segments into an included segment group and an excluded segment group based upon the filtered tissue type matching a tissue type characteristic associated with each of the plurality of segments.

16. The method of claim 13, further comprising determining the filter selection by:
(i) identifying a set of proximate segments from the plurality of segments that are within a configured distance of the position of the virtual camera within the coordinate system, and
(ii) associating the set of proximate segments with a first group of the two or more segment groups, wherein the different visual characteristic of the first group is configured to cause segments in the first group to be excluded from the modified patient model.

17. The method of claim 13, further comprising determining the filter selection by:
(i) identifying a set of intervening segments from the plurality of segments that are positioned along an axis between the virtual camera and a surgical site in the coordinate system, and
(ii) associating the set of intervening segments with a first group of the two or more segment groups, wherein the different visual characteristic of the first group is configured to cause segments in the first group to be excluded from the modified patient model.

18. An image guided surgery system comprising one or more processors configured to:
(i) maintain a coordinate system,
(ii) segment a set of preoperative images to produce a patient model and associate the patient model with the coordinate system, wherein the patient model comprises a three-dimensional model of the patient's anatomy comprised of a plurality of segments,
(iii) identify, for each segment of the plurality of segments, an anatomical structure of the patient corresponding to each segment,
(iii) determine a filter selection indicative of a surgical procedure to be performed on the patient using the image guided surgery system,
(iv) categorize each segment of the plurality of segments into one of two segment groups based upon the filter selection indicative of the surgical procedure and on the anatomical structure corresponding to the respective segment, wherein each of the two segment groups is associated with a different visual characteristic,
(v) render a modified patient model based on the different visual characteristic of each of the two or more segment groups, and
(vi) update the two segment groups by moving a segment categorized into a first segment group to the second segment group based on a present procedural step of the surgical procedure being performed on the patient.

19. The image guided surgery system of claim 18, wherein:
(i) a first visual characteristic associated with the first segment group is configured to cause segments in the first segment group to be included in the modified patient model, and
(ii) a second visual characteristic associated with the second segment group is configured to cause segments in the second segment group to be excluded from the modified patient model.

20. The image guided surgery system of claim 18, wherein to determine the filter selection indicative of a surgical procedure to be performed on the patient comprises to determine a first filter selection, and
wherein the one or more processors are further configured to determine a second filter selection indicative of a tissue type,
wherein to categorize each segment of the plurality of segments further comprises to categorize each segment of the plurality of segments into one of the two segment groups based upon the first filter selection and the second filter selection.

* * * * *